(12) United States Patent
Yamaguchi

(10) Patent No.: US 7,355,093 B2
(45) Date of Patent: Apr. 8, 2008

(54) MODEL ANIMAL WITH OVEREXPRESSION OF REGUCALCIN

(75) Inventor: Masayoshi Yamaguchi, Shizuoka (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 10/804,515

(22) Filed: Mar. 19, 2004

(65) Prior Publication Data

US 2004/0250306 A1 Dec. 9, 2004

Related U.S. Application Data

(63) Continuation-in-part of application No. PCT/JP02/09611, filed on Sep. 19, 2002.

(30) Foreign Application Priority Data

Sep. 20, 2001 (JP) ............................. 2001-287698
Jun. 18, 2002 (JP) ............................. 2002-177666

(51) Int. Cl.
*A01K 67/00* (2006.01)
*A01K 67/033* (2006.01)
*A01K 67/027* (2006.01)

(52) U.S. Cl. ............................................. 800/9; 800/14
(58) Field of Classification Search .................... 800/3, 800/8, 21, 14
See application file for complete search history.

(56) References Cited

FOREIGN PATENT DOCUMENTS

| EP | 0 922 760 | 6/1999 |
|---|---|---|
| JP | 7-97399 | 4/1995 |
| JP | 7-123985 | 5/1995 |
| JP | 10-26623 | 1/1998 |
| JP | 11-9140 | 1/1999 |
| WO | WO 02/34041 | 5/2002 |

OTHER PUBLICATIONS

Yamaguchi et al. (Jun. 24, 2002) J. Cell. Biochem 86:520-529.*
Yamaguchi et al. (2002) Int. J. Mol. Med. 10:377-383.*
Downs et al. (1999) Calcif. Tissue Int 64 :463-469.*
Kolb et al. (1999) Gene 227:21-31.*
Sigmund, C., Jun. 2000 (Arterioscler. Thromb. Vasc. Biol., p. 1425-1429).*
Houdebine, L-M., 2002 (Journal of Biotechnology, vol. 98, p. 145-160).*
Houdebine et al. (2000) Transgenic Research 9:305-320.*
Murray (1999) Theriogenology 51:149-159.*
Ebert et al Mol Endocrinol. 1988; 2(3): 277-83.*
Sordet et al Joint Bone Spine. 2005; 72(6): 503-14.*
Chenug et al Bone. 2006; 39(3): 470-6.*
Mullins et al Nature, 1990, 344; 543-544.*
Hammer et al. Journal of animal Science, 1986, 63, 269-278.*
Mullins et al, EMBO, 1989, 8: 4065-4072.*
Taurog, J. Immunology, 1988, 141: 4020-4023.*
Hammer et al Cell, 1990, 63: 1099-1112.*
Gibbs et al. Nature 428:493-521,2004.
Malakoff. Science 288: 248-253, 2000.
Xu et al. Nat Genet 20: 78-82, 1998.
Ferrari et al. Curr Opin Lipidol 16: 207-213, 2005.
Saftig et al. Proc Natl Acad Sci USA 95: 13453-13458, 1998.
Leheste et al. FASEB J 17:247-249, 2003.
David et al. J Bone Mineral Res 18: 1622-1631, 2003.
Aguirre et al. J Bone Mineral Res 21: 605-615, 2006.
Yamaguchi et al. J Cell Biochem 94: 794-803, 2005.
Haruhiko Inoue, et al., Senescence Marker Protein-30 (SMP30) Enhances The Calcium Efflux From Renal Tubular Epithelial Cells, Clin. Exp. Nephrol (1999) vol. 3, p. 261-267.
Terunobu Ishigami, et al., Regulatory Effects Of Senescence Marker Protein 30 On The Proliferation Of Hepatocytes, Pathology International (2001) vol. 51, p. 491-497.
Hiroyuki Misawa, et al., Suppression Of Cell Proliferation And Deoxyribonucleic Acid Synthesis In Cloned Rat Hepatoma H4-II-E Cells Overexpressing Regucalcin, Journal of Cellular Biochemistry (2002) vol. 84, p. 143-149.
Masayoshi Yamaguchi, The Role Of Regucalcin In Nuclear Regulation Of Regenerating Liver, Biochemical And Biophysical Research Communications (2000) vol. 276, p.

* cited by examiner

*Primary Examiner*—Thaian N. Ton
*Assistant Examiner*—Anoop K. Singh
(74) *Attorney, Agent, or Firm*—Frommer Lawrence & Haug LLP; Thomas J. Kowalski; Deborah L. Lu

(57) ABSTRACT

The present invention provides an animal model which overexpresses regucalcin, a calcium-binding protein that is inherently expressed in the liver and the like of the higher animal, and which is characterized by a showing of bone pathology typified by osteoporosis. When regucalcin expression is lowered, it induces other physiological abnormalities. In the present invention, cDNA encoding the full length of regucalcin protein was cloned from a rat liver cDNA library, ORF was cut out, and introduced into an expression vector (pCXN2). The pCXN2 gene expression vector containing ORF cDNA was microinjected into the male pronucleus of a fertilized egg of rat which was subsequently transplanted into the uterine tube of a host rat to generate transgenic rats homozygous for regucalcin. The transgenic rats are characterized by remarkable bone pathology, morphologically as well as biochemically, and by significant suppression of body weight gain, and are therefore useful for screening of preventive and therapeutic agents related to bone diseases.

2 Claims, 5 Drawing Sheets

MODEL ANIMAL WITH OVEREXPRESSION OF REGUCALCIN

REFERENCE TO RELATED APPLICATIONS

This application is a continuation-in-part of International Application PCT/JP02/09611 filed Sep. 19, 2002 and published as WO 03/026408 on Apr. 3, 2003, which claims priority to Japanese Patent Applications 2001-287698 filed Sep. 20, 2001 and 2002-177666 filed Jun. 18, 2002. Each of the above applications, and each document cited in this text and in each of the above applications ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, nonobvious, inventive, over the prior art, e.g., over documents cited herein or incorporated by reference herein. And, the terms "consists of" and "consisting of" have the meaning ascribed to them in U.S. Patent law; namely, that these terms are closed ended.

TECHNICAL FIELD

The present invention relates to regucalcin gene introduced transgenic non-human animal, more specifically to a transgenic non-human animal to which regucalcin gene is introduced and that has ability to suppress body weight gain, a method of producing regucalcin using said transgenic non-human animal, a screening method of preventive and therapeutic agent of disease caused by the overexpression of regucalcin and a screening method of causative agent of disease caused by the lowering of regucalcin expression. Moreover, the present invention relates to a animal model having bone disease typified by aosteoporosis, more concretely to a animal model selected and determined by morphological measurement evaluation of bone or biochemical measurement evaluation of bone component, from non-human animals overexpressing regucalcin and that shows bone disease such as vulnerability of bone tissue, change of bone morphology, delay in bone growth and the like, and to a screening method of preventive and therapeutic agent of bone disease typified by aosteoporosis by using said animal model having bone diseases.

BACKGROUND

Peptide hormone is bound to the receptor of the cell membrane and transmits the information into the cells. $Ca^{2+}$ plays an important role in this mechanism. Many proteins that binds $Ca^{2+}$ exist in the cells, and calmodulin plays an important role as a protein that amplify that action. It is clarified that $Ca^{2+}$ is bound to said calmodulin, and activates various enzymes related to the regulation of cell functions (Science, 202, 19-27, 1984). Moreover, it is known that $Ca^{2+}$ acts on protein kinase C or other $Ca^{2+}$ binding protein (including enzyme) (Science, 233, 305-312, 1986). Regucalcin is also a $Ca^{2+}$ binding protein that was isolated from rat liver cytoplasm by the present inventor.

Regucalcin is a $Ca^{2+}$ binding protein whose molecular weight is 33388, wherein the $Ca^{2+}$ binding constant shows $4.19 \times 10^5 M^{-1}$, having 6 to 7 high-affinity $Ca^{2+}$ binding sites, comprising 34% of α-helical structure, and is an acidic protein existing notably in liver, wherein the isoelectric point is pI5.20. Regucalcin is a specific protein that does not comprise a site EF hand structure (region) that is seen in calmodulin and many other $Ca^{2+}$ binding proteins. For example, by binding $Ca^{2+}$, the calmodulin increases its α-helical content and its structure becomes robust, but regucalcin decreases the α-helical content. Moreover, on the other hand, it has been clarified that in the regulation of cell functions, regucalcin inhibits the enzyme activation caused by calmodulin and also inhibits the activation of protein kinase C. As described, there are many knowledges such as regucalcin functions as a regulatory protein for signaling (FEBS Lett, 327, 251-255, 1993).

The regucalcin gene exists on chromosome X in rat (Xq 11.1-12), and is localized also in chromosome X in human. The regucalcin gene has been demonstrated in higher animals such as monkey, mouse, dog, bovine, rabbit, chicken and the like other than rat or human, but not yeast, and it is believed that it encodes highly differentiated protein. Regucalcin cDNA is cloned and all of its whole structure is determined (Japanese Laid-Open Patent Application No. 7-123985). As for the rat liver regucalcin cDNA, the base pair encoding whole amino acid is 0.897 kb, and it translates 299 amino acids. Furthermore, the base sequence of regucalcin cDNA of the mouse liver or human liver is also determined, and by comparison with regucalcin cDNA of rat liver, they have 94% and approximately 89% of homology, respectively. The expression of regucalcin mRNA is observed in the liver of human, rat, mouse, bovine, chicken and the like, and in these livers, the presence of regucalcin protein has been also verified.

The regucalcin is known to be a protein characterized as a regulatory protein of intracellular $Ca^{2+}$ signaling having multifunctional role, and to be an important protein related to the regulation of cell functions (Life Sciences 66, 1769-1780, 2000, Biochemical and Biophysical Research Communications 276, 1-6, 2000). It has also been clarified by experiments to animals that the expression of regucalcin in liver or kidney of a living body is decreasing at the time of hepatopathy (Molecular and Cellular Biochemisty 131, 173-179, 1994) or nephropathy (Molecular and Cellular Biochemisty 151, 55-60, 1995), and the relation between regucalcin and cause of disease is suggested. There is a method to differentiate the serum of the patient having liver disease by measuring the serum of concentration of regucalcin, which exists specifically in kidney unlike the existing liver function markers such as GOT, GPT and the like, and as the regucalcin is increasing significantly in the serum of patient having liver disease, but on the other hand, almost no regucalcin is detected in the serum of a healthy person, therefore, said measurement is known to be useful for a differential diagnosis of serum of patient having liver disease (Japanese Laid-Open Patent Application No. 10-26623).

On the other hand, bone tissues are comprised of bone cells and substrates, wherein ⅓ is an organic matter wherein collagen is the major component, and ⅔ is an inorganic substance which is the bone mineral of calcium-phosphate. Structurally, it can be divided in compact substance, spongy substance and cortical substance, and for example, the diaphysis of the long bone is composed of compact sub- stance and the epiphysis is composed of spongy substance surrounded by cortical substance. Bone is not a structure that does not change at all once after it is formed, but its structure and the amount are maintained upon the balance of bone formation and bone resorption. Therefore, in case the balance is disrupted due to aging or other reasons, various bone diseases can be developed. Among bone diseases, as for diseases developed by abnormal increase of bone resorption wherein calcium salt elutes from bone into blood vessel, malignant hypercalcemia caused by myeloma or lymphoma and the like, Paget's disease of bone caused by local bone resorption, and aosteoporosis which is not accompanied by a quality change though the absolute level of the bone is decreasing, and the like. It is known that these diseases entail bone pain and induce vulnerability of bone which can become the cause of bone fracture. These diseases are becoming serious social problem due to the increase of the population of aged person.

Furthermore, non-human mammals having DNA in which exogenous 25-hydroxyl vitamin D324-hydrozylase gene or its mutant gene is integrated, wherein the animals can be used as pathological animal model for bone disease such as hypercalcemia, hypocalcemia, hyperparathyroidism, rickets, osteomalacia, aosteoporosis, osteopenia and the like, kidney disease such as glomerulonephritis, glomerulosclerosis, chronic nephritis, renal failure and the like, malignant tumors, psoriasis or complication thereof and the like, and can be used to perform the clarification of the pathological mechanism and investigation of method of treatment of disease and screening of therapeutic agents, are known (Japanese Laid-Open Patent Application No. 11-9140).

The regucalcin protein is a specific multifunctional protein specifically expressed in liver, which is expressed also with a low level, in kidney, heart, cerebrum (neuron), is engaged with the regulation of the cell function related to intracellular $Ca^{2+}$ signaling. When its expression is lowered, it induces physiological abnormality. A functional analysis has been performed heretofore by using protein or anti-regucalcin monoclonal antibody isolated from rat liver, and the present inventor has clarified functional role of regucalcin in many living body regulation, beside a role as a regulatory factor of calcium signal mentioned above, which are regulation of cell nucleus function such as regulation of calcium transportation enzyme in the cells; a role as an activating factor of protease; regulation of cell nucleus function such as: regulation of calcium transport of cell nucleus; a role in the degradation of cell nucleus DNA; a role in cell nucleus function when regenerating liver; a role in the resorption of calcium in renal tubule and the like.

The present inventor noted during the process of research for clarification of various functional roles of the regucalcin, that the regucalcin has specific effect different from many other $Ca^{2+}$ binding proteins. The inventor perceived that the functional regulation of various cells to which calcium is related is formed on the balance of the expression level of regucalcin in vivo and the expression level of many other $Ca^{2+}$ binding proteins such as calmodulin and the like; and had decided to examine the change and effect occurred in the living body, when the balance of the expression level of regucalcin and the expression level of many other $Ca^{2+}$ binding proteins is disrupted. The object of the present invention is to provide animal model with overexpression of regucalcin, which is a tool to examine how the change and effect occur in a living body, when the balance between regucalcin and many other $Ca^{2+}$ binding proteins is disrupted by overexpressing the regucalcin which is expressed primitively in the liver and the like of higher animals.

Furthermore, conventionally, concerning the calcium bone metabolism which typified by osteoporosis, as for the development of therapeutic agent and prevention of bone pathology occurring frequently in aged person especially in women, spayed rats are used. However, as for spayed animals, surgical extirpation surgery is necessary, and moreover, more than 3 months of breeding are required until the bone mass decrease. Therefore, not only the cost for research becomes expensive, but there are many technical and temporal restrictions. Furthermore, as for other animal models having bone pathology seen in clinical aspect, there are animal models having bone pathology with inflamed (rheumatism) arthritis, but as they are developed by an administration of drug, other side effects are shown and there are physiological problems. The object of the present invention is to provide animal models having bone pathology typified by osteoporosis, that can solve the above mentioned problems wherein surgical removal such as ophotectomy and the like is not necessary, that do not require breeding period until the bone mass decreases, and that do not have physiological problems such as being accompanied by side effects.

The present inventor has made a keen effort to solve the above mentioned problems. The regucalcin cDNA was cloned from rat liver cDNA library, cDNA which encodes the full length of the regucalcin protein was isolated, ORF was cut from said rat regucalcin full length cDNA to be introduced into the expression vector (pCXN2). Said gene expression vector was microinjected into the male proneucleus of the rat fertilized egg, said fertilized egg was transplanted into the uterine tube of the foster parent rat to generate rats. DNA was extracted from the tissue of the generated rats, and rats in which regucalcin cDNA is integrated were determined by PCR. From 29 rats which have been generated, 5 homogeneous rats (4 males, 1 female) expressing regucalcin cDNA were constructed, and the present inventor has found that the weight gain of said transgenic rats were significantly suppressed. Thus, the present invention has been completed.

Furthermore, the present inventor performed morphological measurement estimation of bone (bone density, bone strength, bone thickness of diaphyseal cortex, length of surrounding of cortex) and biochemical measurement estimation of bone component (amount of calcium, alkaline phosphatase activity of the marker enzyme of osteoblast, amount of DNA which is an index of the number of cells in bone tissue), with the use of bone density measurement apparatus pQTC (peripheral Quantitative Computed Tomography) for animal research, to each of the above-mentioned transformed rat that acquired an ability to overexpress regucalcin by being introduced with regucalcin gene, that do not show any disease of bone apparently. He has found that especially in femur, morphologically as well as biochemically, predominant bone pathology such as thinning of bone tissues, change of bone figuration and growth delay of coccyx due to bone resorption (dissolution of bone mineral) caused by the decreasing of bone mass and bone density are shown. He has then determined that the character of pathological model rats with overexpression of regucalcin is stable through many generations and that can bear to industrial production. Thus, he has completed the present invention.

DISCLOSURE OF THE INVENTION

In other words, the present invention relates to a transgenic non-human animal to which a regucalcin gene is introduced and which overexpresses regucalcin (paragraph 1); the transgenic non-human animal according to paragraph 1, wherein straight chain DNA which is arranged in the order of cytomegalovirus-IE enhancer, chicken □-actin promoter, regucalcin gene, rabbit β-glovin poly A signal is introduced (paragraph 2); the transgenic non-human animal according to paragraph 1 or 2, wherein the regulcaltin gene is a gene that encodes protein consisting of amino acid sequence of Seq. ID No. 2 of the sequence listing (paragraph 3); the transgenic non-human animal according to paragraph 3, wherein the gene encoding protein consisting of amino acid sequence of Seq. ID No. 2 of the sequence listing is, a rat regucalcin gene consisting of DNA sequence of Seq. ID No. 1 of the sequence listing (paragraph 4); the transgenic non-human animal according to any of paragraphs 1 to 4, wherein the animal is homozygote (paragraph 5); the transgenic non-human animal according to any of paragraphs 1 to 5, wherein the animal has an ability to suppress the weight gain (paragraph 6); the transgenic non-human animal according to any of paragraphs 1 to 6, wherein the animal is susceptible to dysfunction of cerebrum (paragraph 7); the transgenic non-human animal according to any of paragraphs 1 to 7, wherein the animal is susceptible to insulin independent diabetes (paragraph 8); the transgenic non-human animal according to any of paragraphs 1 to 8, wherein the animal is susceptible to renal hypertension (paragraph 9); the transgenic non-human animal according to any of paragraphs 1 to 9, wherein the animal is susceptible to impairment of tubular reabsorption (paragraph 10); the transgenic non-human animal according to any of paragraphs 1 to 10, wherein the non-human animal is a rat (paragraph 11).

Furthermore, the present invention relates to a method for producing regucalcin, wherein the transgenic non-human animal according to any of paragraphs 1 to 11 is used (paragraph 12); a screening method of preventive and therapeutic agents for diseases caused by the overexpression of regucalcin, wherein the transgenic non-human animal according to any of paragraphs 1 to 11, or tissues, organs or cells derived from the transgenic non-human animal and a test substance are used (paragraph 13); the screening method of preventive and therapeutic agents for diseases caused by the overexpression of regucalcin according to paragraph 13, wherein the test substance is administered to the transgenic non-human animal, and the level of the weight gain of the transgenic non-human animal is measured and estimated (paragraph 14); the screening method of preventive and therapeutic agents for diseases caused by the overexpression of regucalcin according to paragraph 13 or 14, wherein the disease caused by the overexpression of regucalcin is dysfunction of cerebrum (paragraph 15); the screening method of preventive and therapeutic agents for diseases caused by the overexpression of regucalcin according to paragraph 13 or 14, wherein the disease caused by the overexpression of regucalcin is insulin independent diabetes (paragraph 16); the screening method of preventive and therapeutic agents for diseases caused by the overexpression of regucalcin according to paragraph 13 or 14, wherein the disease caused by the overexpression of regucalcin is renal hypertension (paragraph 17); the screening method of preventive and therapeutic agents for diseases caused by the overexpression of regucalcin according to paragraph 13 or 14, wherein the disease caused by the overexpression of regucalcin is impairment of tubular reabsorption (paragraph 18); and a preventive or therapeutic agent for diseases caused by the overexpression of regucalcin obtained by the screening method according to any of paragraphs 13 to 18 (paragraph 19).

Furthermore, the present invention relates to a screening method of causative agents of diseases caused by the lowering of regucalcin expression wherein the transgenic non-human animal according to any of paragraphs 1 to 11, or tissues, organs or cells derived from the transgenic non-human animal and a test substance are used (paragraph 20); the screening method of causative agents of diseases caused by the lowering of regucalcin expression according to paragraph 20, wherein the test substance is administered to the transgenic non-human animal, and the level of the weight loss of the transgenic non-human animal is measured and estimated (paragraph 21); the screening method of causative agents of diseases caused by the lowering of regucalcin expression according to paragraph 20 or 21, wherein the disease caused by the lowering of regucalcin expression is arteriosclerosis myocardial infarction (paragraph 22); the screening method of causative agents of diseases caused by the lowering of regucalcin expression according to paragraph 20 or 21, wherein the disease caused by the lowering of regucalcin expression is myocardial infarction (paragraph 23); and a causative agent of diseases caused by the lowering of regucalcin expression obtained by the screening method according to any of paragraphs 20 to 23 (paragraph 24).

Moreover, the present invention relates to an animal model having bone pathology wherein the animal model is a non-human animal that overexpresses regucalcin and shows bone pathology (paragraph 25); the animal model having bone pathology according to paragraph 25, wherein the animal expresses one or more bone pathology of any of vulnerability of bone tissue, change of bone morphology or delay in bone growth (paragraph 26); the animal model having bone pathology according to paragraph 25 or 26, wherein the animal is selected and determined among non-human animal that overexpresses regucalcin by a morphological measurement estimation of bone and/or a biochemical measurement estimation of bone component (paragraph 27); the animal model having bone pathology according to paragraph 27, wherein the morphological measurement estimation of bone is one or more measurement estimations of any of bone density, bone strength, bone thickness of diaphyseal cortex or length of surrounding of cortex (paragraph 28); the animal model having bone pathology according to paragraph 27, wherein the biochemical measurement estimation of bone component is one or more measurement estimations of any of amount of calcium, alkaline phosphatase activity or amount of DNA in bone tissues (paragraph 29); the animal model having bone pathology according to any of paragraphs 25 to 29, wherein the characteristic of bone pathology is stable through many generations (paragraph 30); the animal model having bone pathology according to any of paragraphs 25 to 30, wherein the non-human animal that overexpresses regucalcin is a transgenic non-human animal to which regucalcin gene is introduced (paragraph 31); the animal model having bone pathology according to any of paragraphs 26 to 32, wherein the non-human animal that overexpresses regucalcin is homozygote (paragraph 32); the animal model having bone pathology according to any of paragraphs 25 to 32, wherein the non-human animal that overexpresses regucalcin is a female non-animal (paragraph 33); the animal model having bone pathology according to any of paragraphs 25 to 33, wherein the non-human animal that overexpresses regucalcin is a rat (paragraph 34).

Furthermore, the present invention relates to a screening method of preventive and therapeutic agents for bone diseases wherein a test substance is administered to a animal model having bone pathology according to any of paragraphs 25 to 34, and a morphological measurement estimation of bone and/or a biochemical measurement estimation of bone component of the animal model having bone pathology are performed (paragraph 35); the screening method of preventive and therapeutic agents for bone disease according to paragraph 35, wherein the morphological measurement estimation of bone is one or more measurement estimations of any of bone density, bone strength, bone thickness of diaphyseal cortex or length of surrounding of cortex (paragraph 36); the screening method of preventive and therapeutic agents for bone disease according to paragraph 35, wherein the biochemical measurement estimation of bone component is one or more measurement estimations of any of amount of calcium, alkaline phosphatase activity or amount of DNA in bone tissues (paragraph 37); the screening method of preventive and therapeutic agents for bone disease according to any of paragraphs 35 to 37, wherein the bone disease is osteoporosis (paragraph 38); and a preventive or therapeutic agent for bone disease obtained by the screening method according to any of paragraphs 35 to 38 (paragraph 39).

BEST MODE OF CARRYING OUT THE INVENTION

Figure 1:
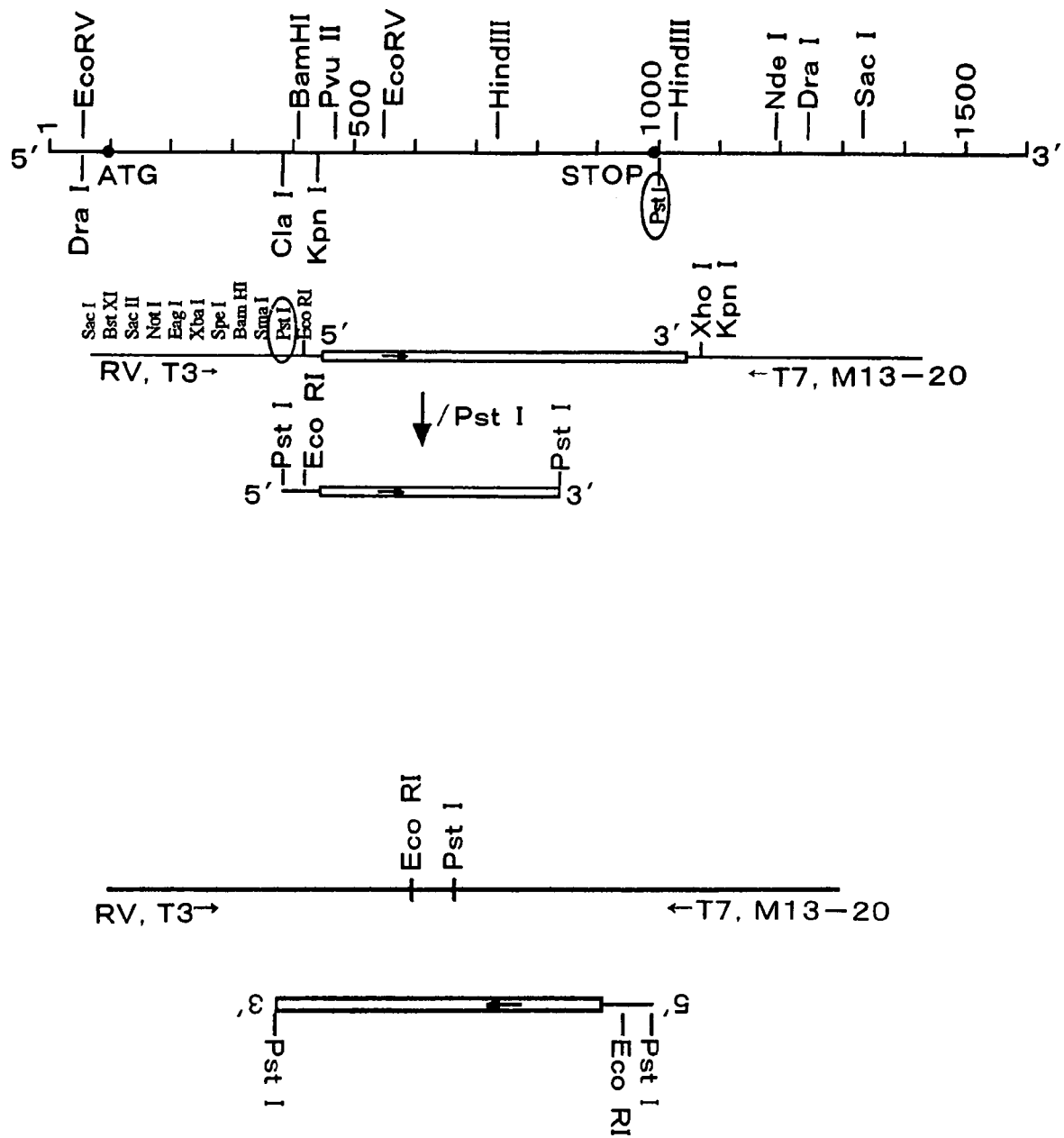
FIG. 1 is a figure that shows the process of cutting the ORF part from the full length cDNA of rat regucalcin, during the construction of the expression vector to generate the transgenic rat of the present invention.

As for the transgenic non-human animal of the present invention, there is no specific limitation as long as it is a non-human animal to which the regucalcin gene is introduced and that overexpresses regucalcin. In the present invention, by the term "overexpress regucalcin", it means that a significantly larger amount of regucalcin is expressed compared to the expression level of regucalcin in wild-type non-human animal. Furthermore, as for non-human animal mentioned above, examples include rat, mouse, bovine, porcine, chicken, frog, human, dog, rabbit and the like, but rat is preferable among these examples. As for mouse that is frequently used as animal model, the organs are small and there is sometime a limit for analysis of pathology, but it is possible in rat to measure for example blood pressure and the like, and it is significantly useful as a means for animal experiments for clarification of pathology or gene therapy.

As for a preferred embodiment for the transgenic non-human animal of the present invention, a transgenic non-human animal to which the straight chain DNA arranged in the order of cytomegalovirus-IE enhancer, chicken β-actin promoter, regucalcin gene, rabbit β-globin poly A signal is introduced can be exemplified. For example, when an expression vector (pCXN2) having marker gene, cytomegalovirus-IE enhancer, chicken β-actin promoter, cDNA insertion site, rabbit β-globin poly A signal and the like to which regucalcin full length cDNA is introduced is used, a transgenic non-human animal can be obtained effectively.

Moreover, as a preferred embodiment for the transgenic non-human animal of the present invention, a transgenic non-human animal wherein the regucalcin gene is a gene that encodes protein consisting of the amino acid sequence of Seq. ID No. 2 of the sequence listing, especially wherein the gene that encodes protein consisting of amino acid sequence of Seq. ID No. 2 of the sequence listing is a rat regucalcin gene consisting of DNA sequence of Seq. ID No. 1 of the sequence listing can be exemplified, but the origin of the regucalcin gene is not limited to rat, and examples include mouse, bovine, porcine, chicken, frog, human, dog, rabbit and the like.

Also contemplated by the present invention is a transgenic non-human animal wherein the regucalcin gene is a gene that encodes protein which comprises a homologue, derivative, variant or fragment of the amino acid sequence of Seq. ID No. 2 wherein the homologue, derivative, variant or fragment thereof has at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% homology to SEQ ID No: 2.

Furthermore, it is also contemplated by the present invention that the gene which encodes the protein of Seq. ID NO: 2 or a protein homologous thereto comprises a homologue, variant, derivative or fragment of the DNA sequence of Seq. ID NO: 1, wherein the homologue, derivative, variant or fragment thereof has at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% homology to SEQ ID No: 1, or is complementary thereto.

Sequence identity with respect to any of the sequences presented here can be determined by a simple "eyeball" comparison (i.e. a strict comparison) of any one or more of the sequences with another sequence to see if that other sequence has, for example, at least 70% sequence identity to the sequence(s).

Alternatively, relative sequence identity can also be determined by commercially available computer programs that can calculate % identity between two or more sequences using any suitable algorithm for determining identity, using for example default parameters. A typical example of such a computer program is CLUSTAL. Other computer program methods to determine identify and similarity between the two sequences include but are not limited to the GCG program package (Devereux et al 1984 Nucleic Acids Research 12: 387) and FASTA (Atschul et al 1990 J Molec Biol 403-410).

The sequence identity or percent homology for proteins and nucleic acids can also be calculated as $(N_{ref}-N_{dif})\times 100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$).

Percent homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is –12 for a gap and –4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (Ausubel et al., 1999 ibid, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied. It is preferred to use the public default values for the GCG package, or in the case of other software, the default matrix, such as BLOSUM62.

Advantageously, the BLAST algorithm is employed, with parameters set to default values. The BLAST algorithm is provided by the National Center for Biotechnology Information (NCBI). The search parameters are defined as follows, can be advantageously set to the defined default parameters.

Advantageously, "substantial identity" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (Karlin and Altschul 1990, *Proc. Natl. Acad. Sci. USA* 87:2264-68; Karlin and Altschul, 1993, *Proc. Natl. Acad. Sci. USA* 90:5873-7) with a few enhancements. The BLAST programs are tailored for sequence similarity searching, for example to identify homologues to a query sequence. For a discussion of basic issues in similarity searching of sequence databases, see Altschul et al (1994) Nature Genetics 6:119-129.

The five BLAST programs perform the following tasks: blastp—compares an amino acid query sequence against a protein sequence database; blastn—compares a nucleotide query sequence against a nucleotide sequence database; blastx—compares the six-frame conceptual translation products of a nucleotide query sequence (both strands) against a protein sequence database; tblastn—compares a protein query sequence against a nucleotide sequence database dynamically translated in all six reading frames (both strands); tblastx—compares the six-frame translations of a nucleotide query sequence against the six-frame translations of a nucleotide sequence database.

BLAST uses the following search parameters:

HISTOGRAM—Display a histogram of scores for each search; default is yes. (See parameter H in the BLAST Manual).

DESCRIPTIONS—Restricts the number of short descriptions of matching sequences reported to the number specified; default limit is 100 descriptions. (See parameter V in the manual page).

EXPECT—The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF—Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUT-OFF values are more stringent, leading to fewer chance matches being reported. (See parameter S in the BLAST Manual). Typically, significance thresholds can be more intuitively managed using EXPECT.

ALIGNMENTS—Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

MATRIX—Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND—Restrict a TBLASTN search to just the top or bottom strand of the database sequences; or restrict a BLASTN, BLASTX or TBLASTX search to just reading frames on the top or bottom strand of the query sequence.

FILTER—Mask off segments of the query sequence that have low compositional complexity, as determined by the SEG program of Wootton & Federhen (1993) Computers and Chemistry 17:149-163, or segments consisting of short-periodicity internal repeats, as determined by the XN U program of Clayerie & States (1993) Computers and Chemistry 17:191-201, or, for BLASTN, by the DUST program of Tatusov and Lipman. Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNN") and the letter "X" in protein sequences (e.g., "XXXXXXXXX").

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi—Causes NCBI gi identifiers to be shown in the output, in addition to the accession and/or locus name.

Most preferably, sequence comparisons are conducted using the simple BLAST search algorithm provided by NCBI. In some embodiments of the present invention, no gap penalties are used when determining sequence identity.

Moreover, as for a preferred embodiment of the transgenic non-human animal of the present invention, a transgenic non-human animal that is homozygote can be exemplified. Said homogeneous that has homo on mutant chromosome can be generated by intercrossing non-human animals such as rats and the like having hetero on chromosome, and as the expression level of regucalcin is larger than heterozygote it is especially preferable for animal models used for experiments. Moreover, as for the transgenic non-human animal of the present invention, a transgenic non-human animal wherein the weight gain is significantly suppressed compared to wild-type non-human animal, in other words transgenic non-human animals having ability to suppress weight gain can be exemplified preferably. It was not possible at all to estimate that a transgenic non-human animal to which regucalcin gene is introduced and that overexpresses regucalcin has said ability to suppress weight gain, and from this new knowledge, it is suggested there is a possibility that regucalcin has a utility as preventive for obesity. From said new knowledge, the transgenic non-human animal of the present invention is a transgenic non-human animal wherein the regucalcin gene is introduced and that overexpresses regucalcin, and has ability to suppress weight gain.

As for a preferred embodiment of the transgenic non-human animal of the present invention, a transgenic non-human animal expressing one or more of the following symptoms or diseases caused by overexpression of regucalcin: symptom of dysfunction of cerebrum, symptom of insulin independent diabetes, symptom of renal hypertension, symptom of impairment of tubular reabsorption and the like. It is believed that the dysfunction of cerebrum is developed by that the overexpressed regucalcin suppresses the activation of Ca-calmodulin dependent protein kinase that is necessary for the mechanism of cerebrum to maintain memory, and controls the neurotransmission in neuron. Therefore, the transgenic non-human animal of the present invention is useful as an experiment animal model for dysfunction of cerebrum such as memory (dementia such as Alzheimer disease and the like). Moreover, regucalcin expresses in kidney or liver, controls the intracellular signaling of the hormone, and due to the overexpression of regucalcin, the action expression of the hormone controlling the function of the liver and the kidney is impaired, and in the liver, as the function of insulin is suppressed, the insulin independent diabetes is induced. Furthermore, in the kidney, it is believed to induce renal hypertension related to the renin-angiotension system, and moreover the impairment of tubular reabsorption related to the metabolism of electrolyte. Therefore, the transgenic non-human animal of the present invention is useful as an experiment animal model of insulin independent diabetes, renal hypertension, impairment of tubular reabsorption and the like.

As for the method for establishing animal models such as model rats and the like, having ability to suppress weight gain, of the present invention, a method using the method for preparing transgenic animals which is already known (for example, Proc. Natl. Acad. Sci. USA 77:7380-7384, 1980) can be exemplified. For example, as for a method for generating a regucalcin (RC) transgenic rat, a method as follows or the like can be exemplified: the regucalcin cDNA is cloned from rat liver cDNA library, cDNA which encodes the full length of regucalcin protein is isolated, open reading frame (ORF) is cut from said rat regucalcin full length DNA to be introduced into the expression vector, a straight chain DNA fragment comprising a transgene prepared by linealizing said gene expression vector is microinjected into the male pronucleus of the rat fertilized egg, and said fertilized egg or the embryo of 2 cells period is transplanted to the uterine tube of the foster parent rat to generate rats, and DNA is extracted from the tissue of the generated rats to determine by PCR that regucalcin cDNA is integrated.

As for the method for preparing regucalcin of the present invention, there is no specific limitation as long as it is a method using a transgenic non-human animal of the present invention, preferably a homozygous transgenic non-human animal. For example by removing the liver from a homozygous regucalcin transgenic rat, the regucalcin can be isolated and purified from the homogenate according to a method described previously (Chem. Pharm. Bull. 26, 1915-1918, 1978). Moreover, for the purpose of yield increase of the regucalcin, calcium, calcitonin, insulin, estrogen and the like can be administered to transgenic non-human animals.

As for the screening method of preventive and therapeutic agents for diseases caused by overexpression of regucalcin of the present invention, there is no specific limitation as long as it is a method that uses a transgenic non-human animal of the present invention or tissues, organs or cells derived from the transgenic non-human animal and test substances, and as for diseases caused by overexpression of regucalcin, examples include dysfunction of cerebrum, insulin independent diabetes, renal hypertension, impairment of tubular reabsorption and the like. As for the method of using transgenic non-human animal and test substance as described above, examples include: a method of administering directly test substances to transgenic non-human animals, measuring and estimating the level of weight gain of transgenic non-human animals, and the level of diseases caused by the overexpression of regucalcin; a method of measuring and estimating the level of suppression of regucalcin expression in tissues, organs or cells obtained from the transgenic non-human animal after test substances were administered; and a method of estimating the morphological change in tissues or organs by immunostaining with monoclonal antibody or by using electron microscope, and the like. As for a method using tissues, organs or cells derived from the transgenic non-human animal and test substances, examples include: a method of culturing tissues, organs or cells derived from transgenic non-human animals under the presence of test substances, then measuring and estimating the level of suppression of regucalcin expression in said tissues, organs or cells; and a method of estimating the morphological change in tissues or organs by immunostaining with monoclonal antibody or by using electron microscope, and the like.

As for tissues or organs described above, liver, renal tubule, heart, cerebrum and the like can be exemplified concretely, and as for cells, hepatocytes or neurons constituting these tissues or organs can be exemplified concretely. Moreover, when screening these, it is preferable to compare and estimate with wild-type non-human animal, especially with litter wild-type non-human animal, as it enables to perform accurate comparative experiment at individual level. By this way, according to the screen method of the present invention described above, it is possible to screen preventive or therapeutic agents for diseases caused by the overexpression of regucalcin such as dysfunction of cerebrum, insulin independent diabetes, renal hypertension, impairment of tubular reabsorption and the like, and the preventive or therapeutic agents obtained by said screening method are included in the scope of the present invention.

As for the screening method of causative agents of diseases caused by the lowering of regucalcin expression of the present invention, there is no specific limitation as long as it is a method using the transgenic non-human animal of the present invention, or tissues, organs or cells derived from the transgenic non-human animal and a test substance, and as for diseases caused by the lowering of regucalcin expression, arteriosclerosis, myocardial infarction and the like can be exemplified. As for the method using transgenic non-human animals described above and a test substance, examples include: a method of administering directly test substances to transgenic non-human animals, then measuring and estimating the level of weight loss of transgenic non-human animals and the level of disease caused by the lowering of regucalcin expression; a method of measuring and estimating the level of increase of regucalcin expression in tissues, organs or cells obtained from the transgenic non-human animal after being administered test substances; and a method of estimating the morphological change in tissues or organ by immunostaining with monoclonal antibody or by using electron microscope, and the like. As for a method using tissues, organs or cells derived from the transgenic non-human animal and a test substance, examples include: a method comprising the step of culturing tissues, organs or cells derived from transgenic non-human animals under the presence of a test substance, then measuring and estimating the level of increase of regucalcin expression in said tissues, organs and cells; and a method of estimating the morphological change in tissues or organs by immunostaining with monoclonal antibody or by using electron microscope, and the like.

As for tissues or organs described above, liver, renal tubule, heart, cerebrum and the like can be exemplified concretely, and as for cells, hepatocytes or neurons constituting these tissues or organs can be exemplified concretely. Moreover, when screening these, it is preferable to compare and estimate with wild-type non-human animal, especially with litter wild-type non-human animal, as it enables to perform accurate comparative experiment at individual level. By this way, according to the screening method of the present invention described above, it is possible to screen preventive or therapeutic agents for diseases caused by the lowering of regucalcin expression such as arteriosclerosis, myocardial infraction and the like. The causative agents of disease caused by the lowering of regucalcin expression obtained by said screening method is useful to further clarify the action and role of regucalcin in the living body. Furthermore, by screening substances inhibiting its action, such as substances binding to these causative agents, it is also useful as there is a possibility to develop preventive or therapeutic agents for diseases caused by the lowering of regucalcin expression, and therefore, said causative agents are also included in the scope of the present invention.

Next, as for animal models having bone pathology of the present invention, there is no specific limitation as long as it is a non-human animal that overexpresses regucalcin and shows bone pathology, and as for said animal models having bone pathology, a transgenic non-human animal of the present invention to which regucalcin gene is introduced as described above, can be preferably exemplified. Therefore, animal models having bone pathology and the screening method of preventive or therapeutic agents of the present invention will be explained in the following, but in more details, it can be referred to the description concerning the transgenic non-human animal of the present invention described above or the screening method of preventive or therapeutic agents for diseases caused by the overexpression of regucalcin of the present invention and the like. In the meantime, by bone pathology in the present invention, it refers to a condition wherein bone or its growth is not normal due to the decreasing of bone amount, vulnerability of bone tissues, change of bone morphology, delay in bone growth and the like, caused by abnormality of calcium bone metabolism and the like typified by osteoporosis.

As for animal models having bone pathology of the present invention described above, it is preferable to be a animal model having bone pathology showing one or more of any bone pathology of vulnerability of bone tissues, change of bone morphology, delay in bone growth, that has been selected and determined from non-human animals overexpressing regucalcin by one or more measurement estimation from any morphological measurement estimation of bone, for example bone density, bone strength, thickness of diaphyseal cortex, length of surrounding of cortex and/or one or more measurement estimation from any biochemical measurement estimation of bone component, for example amount of calcium, activation of alkaline phosphatase, amount of DNA in bone tissues. For the morphological measurement estimation of bone described above, the bone density measuring apparatus pQTC (peripheral Quantitative Computed Tomography) for animal research (Bone Vol. 29, No. 2, August 2001; 101-104) can be used particularly advantageously. The biochemical measurement estimation of bone components can be performed by a common method in this field such as described in the examples hereinafter. However, as for the morphological measurement estimation of bone or biochemical measurement estimation of bone components, test animals that needs the bone itself such as femur and the like, can not be used directly as animal models having bone pathology. Therefore, animal models having bone pathology selected and determined mentioned above refer to litter animals of animals used for morphological measurement estimation of bone or biochemical measurement estimation of bone components or its offspring.

For example, as described previously, a DNA fragment cut from the rat regucalcin expression vector made by the present inventor and being linealized, is microinjected into follicular cells of the fertilized eggs being prepared separately, the ovum are cultured, the embryo wherein no abnormality is observed after development are transplanted into the uterine tube of foster parent. Animal models having bone pathology of the present invention can be selected and determined by performing to the generated rats, morphological measurement estimation of bone and biochemical measurement estimation of bone components especially by using pQTC bone density measurement apparatus for animal research. Among these, animal models wherein the characteristic of bone pathology is stable through many generations, and appropriate for commercial production are preferable. Furthermore, as for animal models having bone pathology of the present invention, regucalcin transgenic animal model having bone pathology which is homozygote can be preferably exemplified. As for said homozygote having homo on mutant chromosome, it can be obtained by intercrossing non-human animals such as rats and the like, having hetero on chromosome, and as the expression level of regucalcin is larger than the heterozygote, it is preferable as the characteristic of bone pathology such as change of bone is strongly expressed. Moreover, as for the animal model having bone pathology of the present invention, female animal models having bone pathology such as female rats and the like can be preferably exemplified as the regucalcin gene is on the X chromosome, and the characteristic of bone pathology such as change of bone and the like is expressed more significantly in female more than male.

As for the screening method of preventive and therapeutic agents for bone pathology of the present invention, there is no specific limitation as long as it is a screening method wherein a test substance is administered to animal models having bone pathology of the present invention, and a morphological measurement estimation of bone and/or biochemical measurement estimation of bone component is performed to said animal models having bone pathology. As for test substance, beside synthetic compounds, peptide, protein and the like that are already known, for example extracted tissue of mammals, supernatant of cell culture and the like, or various extract component of plants and the like are used. For example, by administering orally or parenterally test compounds to animal models having bone pathology of the present invention, and performing morphological measurement estimation of bone such as for example bone density, bone strength, bone thickness of diaphyseal cortex or length of the surrounding of cortex and the like, or biochemical measurement estimation of bone component such as for example amount of calcium, alkaline phosphatase activity, amount of DNA in bone tissues and the like, in the animal model having bone pathology, the preventive or therapeutic agent for bone pathology such as osteoporosis and the like can be screened. Moreover, when screening these, it is preferable to compare and estimate with wild-type non-human animal, especially with litter wild-type non-human animal, as an accurate comparative experiment can be performed at an individual level.

As for the preventive and therapeutic agents for bone pathology of the present invention, there is no specific limitation as long as it is a preventive or therapeutic agent for bone pathology obtained by a screening method of the present invention described above, and in case that these preventive or therapeutic agents are used as drugs, various prescribed compounds such as pharmaceutically acceptable normal carrier, bonding agent, stabilizing agent, excipient, diluent, pH buffer agent, disintegrator, solubilizer, dissolving adjuvant, isotonic agent and the like can be added.

Specifically, the active ingredient(s) of a pharmaceutical composition is contemplated to exhibit excellent therapeutic activity, for example, in the treatment of bone pathologies of the present invention. Dosage regimes may be adjusted to provide the optimum therapeutic response. For example, several divided doses may be administered daily or the dose may be proportionally reduced as indicated by the exigencies of the therapeutic situation. Dosages may be administered at intervals of the course of several days, weeks, months or years.

The active compound may be administered in a convenient manner such as by the oral, intravenous (where water soluble), intramuscular, subcutaneous, intranasal, intradermal or suppository routes or implanting (e.g. using slow release molecules). The method of administration may depend on factors such as the location of the cancer or other ailment in the body which is to be treated. Depending on the route of administration, the active ingredient may be required to be coated in a material to protect said ingredients from the action of enzymes, acids and other natural conditions which may inactivate said ingredient.

In order to administer the combination by other than parenteral administration, it will be coated by, or administered with, a material to prevent its inactivation. For example, the combination may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin.

Liposomes include water-in-oil-in-water CGF emulsions as well as conventional liposomes.

The active compound may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilisation. Generally, dispersions are prepared by incorporating the sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the combination of polypeptides is suitably protected as described above, it may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. The amount of active compound in such therapeutically useful compositions in such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired.

Acceptable carriers or diluents for therapeutic use are well known in the pharmaceutical art, and are described, for example, in Remington's Pharmaceutical Sciences, Mack Publishing Co. (A. R. Gennaro edit. 1985).

The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

As for a method for preventing or treating bone pathology such as aosteoporosis and the like by using these preventive or therapeutic agents, preventive or therapeutic agents mentioned above with the appropriate dose according to the patient's sex, body weight, symptoms, can be administered orally or parenterally. In other words, it can be administered orally in a dosage form used generally, for example in form of powder, granule, capsules, syrup, suspension and the like, or parenterally for example in form of solution, emulsion, suspension and the like by injection, and moreover, it can be administered in nostril in form of spray.

The present invention will be explained in detail with examples in the following, but the technical scope of the present invention is not limited to these examples.

EXAMPLES

Example 1

Preparation of Rat RC cDNA (Preparation of RNA)

Liver was extracted from a male Wistar rat (3 weeks old), and homogenized with guanidine-isothiocyanate solution (4M guanidium thiocyanate, 25 mM sodium citrate (pH 7.0), 0.5% sarcosyl, 0.1 M 2-mercaptoethanol and 2 M sodium acetate). This mixture was extracted with phenol-chloroform-isoamyl alcohol mixed solution, and centrifuged at 4° C., 10,000×g for 20 minutes. Isopropanol was added to the aqueous layer, left at −20° C. to precipitate RNA. The precipitate was recovered, and dissolved in 0.5% sodium dodecyl sulfate treated with diethylpyrocarbonate. The resultant was put in an olygo (dT) cellulose column to purify poly (A)+RNA.

(Preparation of cDNA Library)

50 units of Moloney-Murine Leukemia virus reverse transcriptase and oligo (dT) 18 primer linker were added to purified poly (A)+RNA (5 μg), to synthethize a single-strand cDNA. E. coli RNase H and DNA polymerase I were added to said synthethized single-strand cDNA to synthethize double-strand cDNA. EcoRI adapter was added to this, and connected with phage expression vector (λZAPII) which was previously digested with XhoI and EcoRI. Further, by using packaging extract, the phage of cDNA library packaged to phage was prepared.

(Selection of RC cDNA Clone)

Approximately 1×10$^6$ of phage of rat liver cDNA library was mixed with E. Coli, and planted in 20 agar plates. After incubation at 42° C. for 3 hours and half, the nitrocellulose membrane treated with 10 mM isopropyl thio β-D-galactoside was placed on the plate, and was incubated at 37° C. for 3 hours and half. The nitrocellulose membrane was blocked, and then incubated with anti RC rabbit serum (×200) at room temperature for 2 hours. The membrane was washed and then alkaline phosphatase conjugated anti-rabbit IgG antibody was added for incubation. The resultant was submerged in a coloring solution (0.35 mM nitroblue tetrazolium, 0.4 mM 5-bromo-4-chloro-3-Indolyl Phosphate) for coloring, and RC cDNA positive plaque was identified.

(Subcloning to Plasmid Vector)

Phage vector λZAPII includes the base sequence of pBluescript being the plasmid vector in its sequence. The RC cDNA fragment cloned in λZAPII was inserted into this pBluescript. Moreover, at the both ends of pBluescript, an initiation point and termination point of replication of helper phage exist. The phage was isolated from the plaque determined here, was infected with E. Coli SURE and R408 helper phage, pBluescript including RC cDNA fragment was synthethized inside E. Coli, and was released outside E. Coli in form of helper phage. This phage solution was further infected with E. Coli SURE, and replicated in the fungus as a plasmid having RC cDNA fragment. This E. Coli was implanted to LB plate comprising 50 μg/ml of Ampicillin and ampicillin-resistant colony was selected.

(Determination of the Base Sequence of cDNA Insert)

All of the base sequence of cDNA insert was determined by using Sequenase system (US Biochemical). In other words, plasmid DNA was truncated with EcoRI, the fragment was alkalinized degeneratively and added with a primer and annealed. The resultant was divided in 4 after added with 35S dCTP, 0.1 M DTT, enzyme solution for sequenase solution. ddATP, ddGTP, ddTTP, ddCTP were added to each, and incubated at 37° C. for 5 minutes. The resultants were isolated by electrophoresis on acrylamide gel, the autoradiography to read the base sequence was performed. All of the base sequence of regucalcin cDNA is shown in Seq. ID No. 1. Further, the amino sequence obtained is also shown in Seq. ID No. 2. The molecular weight of regucalcin calculated from this, was 33,388. This value was the same with the one calculated with regucalcin purified by the electrophoresis on SDS polyacrylamide.

Example 2

Generation of Transgenic Rat (Construction of Transgene)

Figure 2:
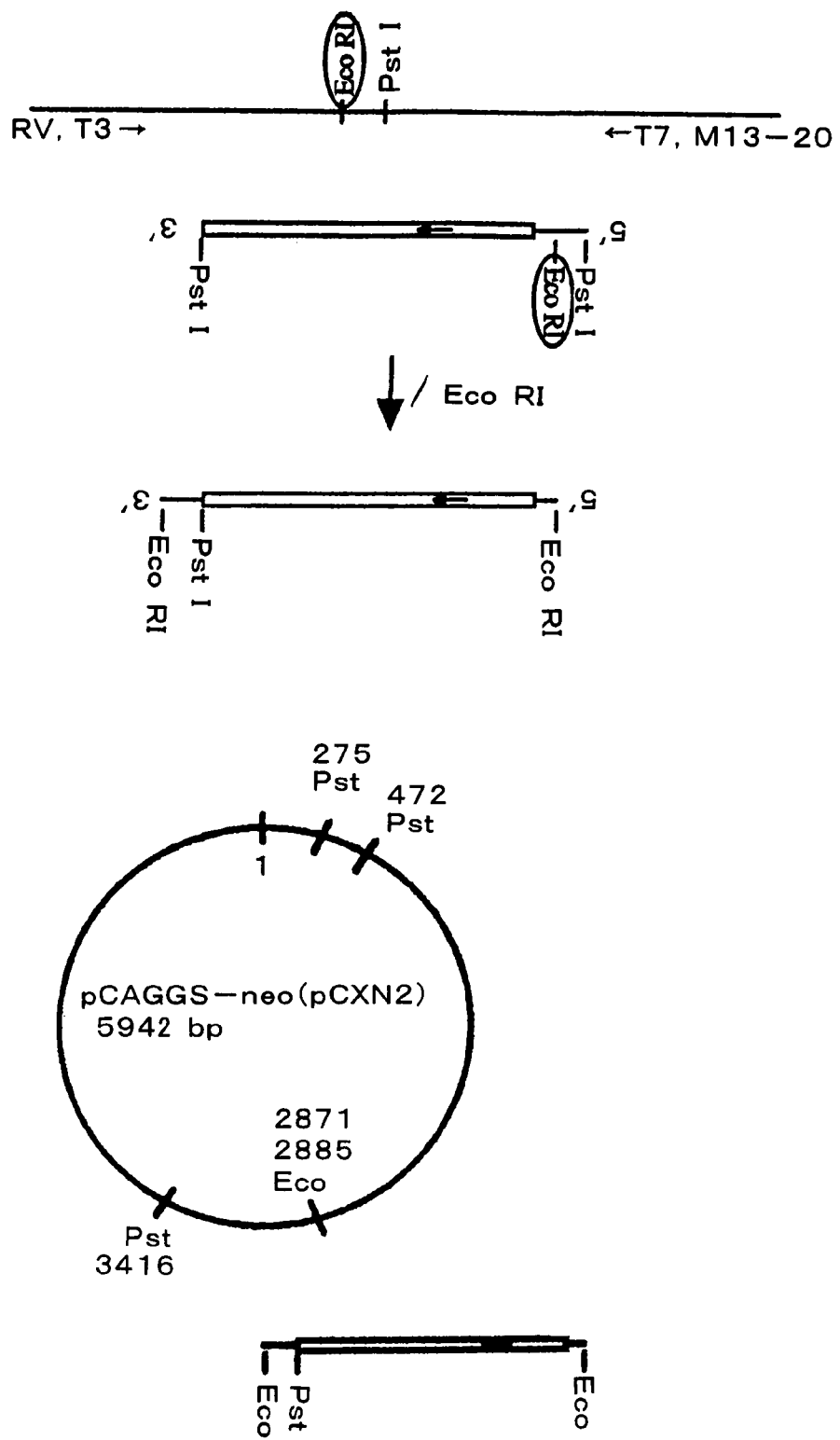
FIG. 2 is a figure that shows the process of introducing the ORF part of the full length cDNA of rat regucalcin into the expression vector pCXN2, during the construction of the expression vector to generate the transgenic rat of the present invention.
Figure 3:
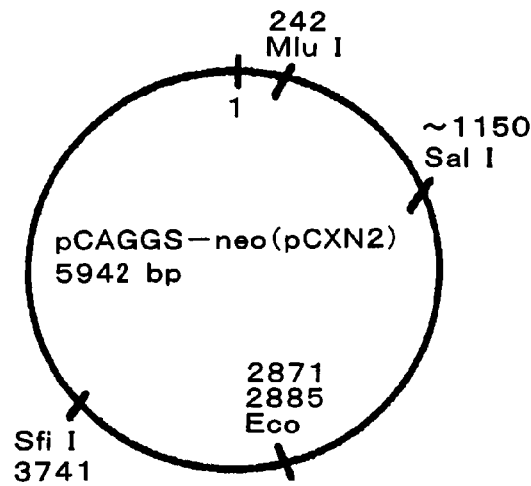
FIG. 3 is a figure that shows the process of preparing the transgene fragment that has been linealized to generate the transgenic rat of the present invention.
Figure 3:
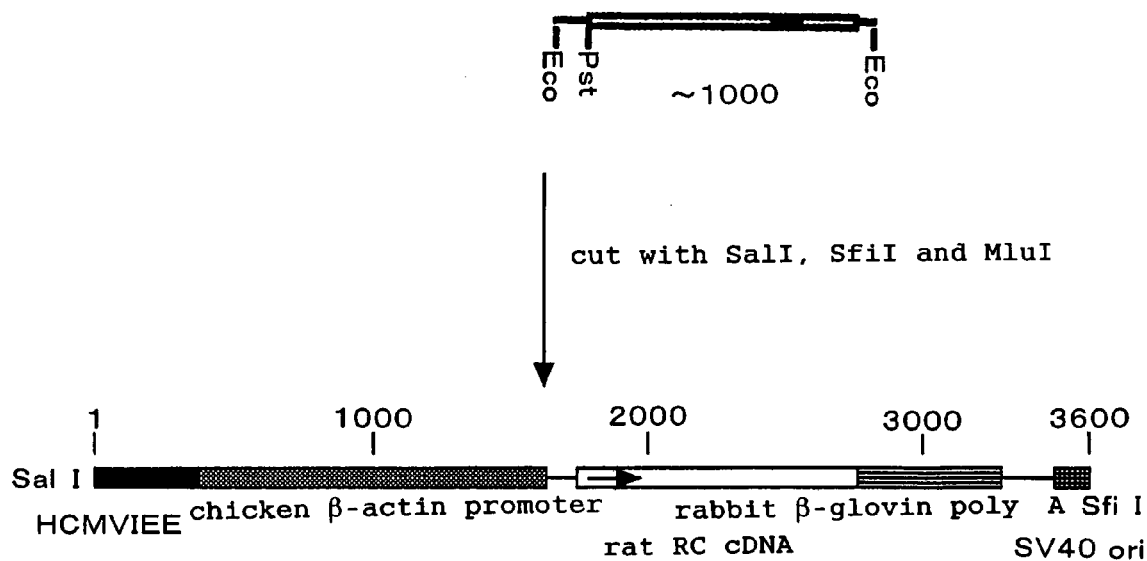
Figure 4:
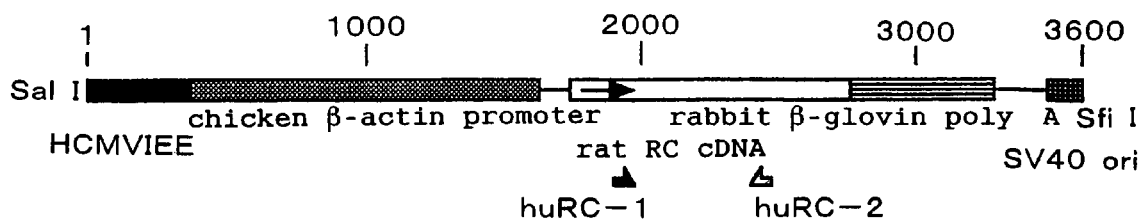
FIG. 4 is a figure that shows the position of the primer during determination by PCR of the regucalcin gene in the transgenic rat of the present invention.
Figure 5:
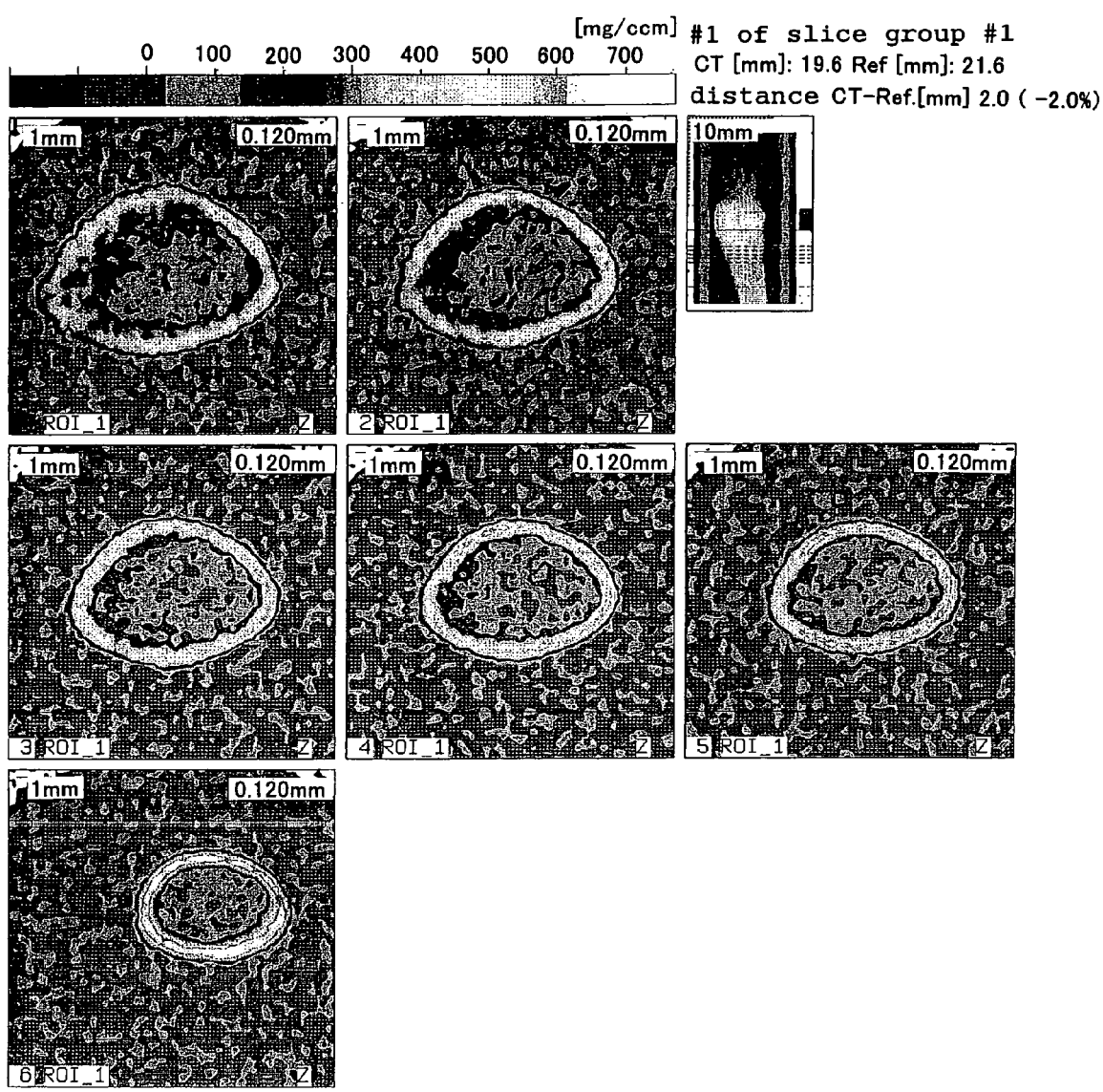
FIG. 5 is a figure that shows the result of scanning the femur tissues (metaphysic part and diaphysis part) of the model rats having bone pathology of the present invention, by using pQTC bone density measurement apparatus for animal research.
Figure 6:
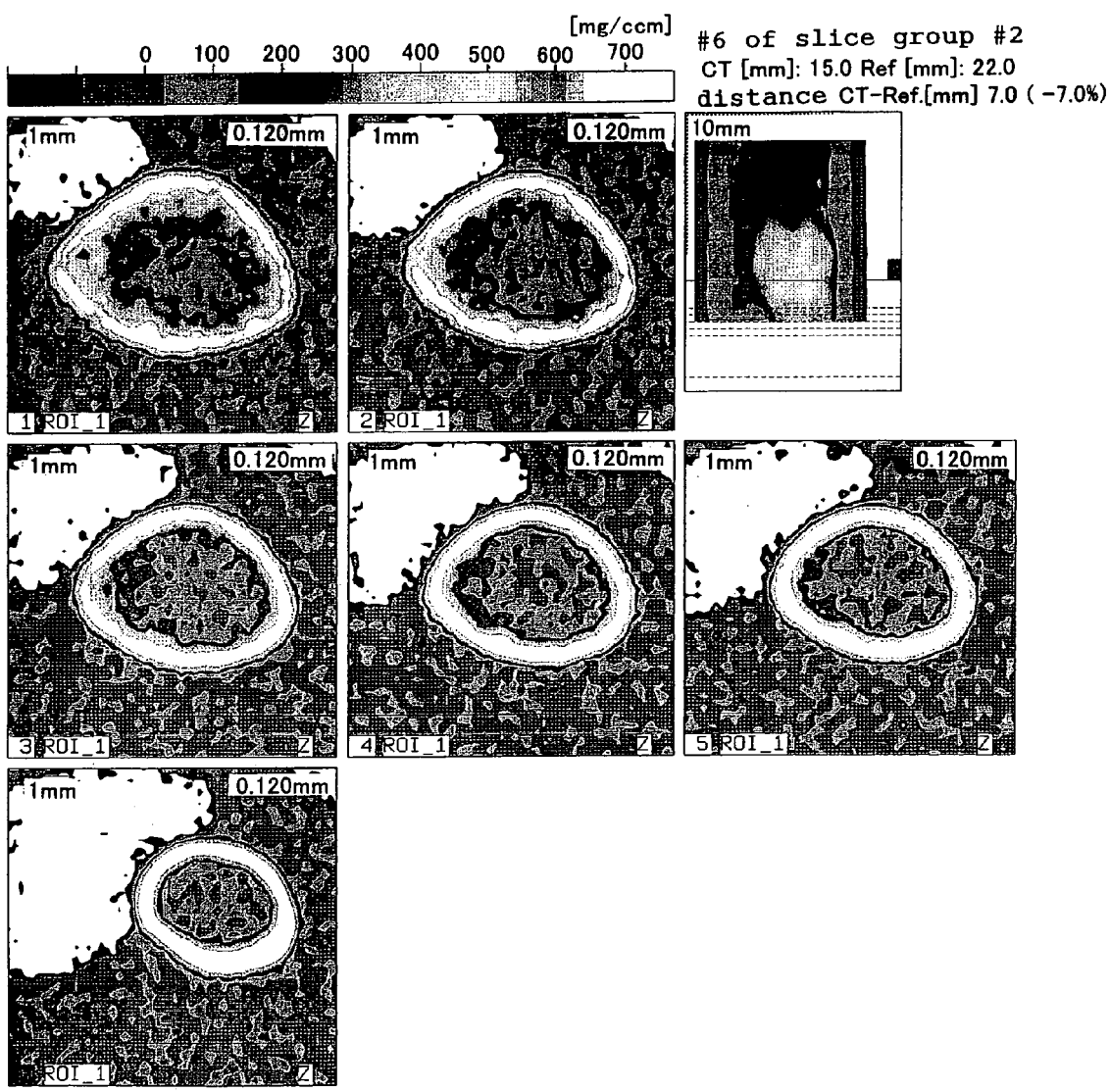
FIG. 6 is a figure that shows the result of scanning the femur tissues (metaphysic part and diaphysis part) of SD wild-type normal rat which is the control, by using pQTC bone density measurement apparatus for animal research.

From the plasmid containing rat regucalcin full length cDNA obtained in Example 1, RC-900 (glycerol stock; RC-F), vector pBluescript SK (−), DNA fragment containing all ORF was resected with PstI (FIG. 1A). Said PstI fragment resected was integrated into PstI site of pBluescript II KS (+) (FIG. 1B). Then, EcoRI fragment obtained by resecting with EcoRI (FIG. 2A) was introduced into EcoRI site of the expression vector pCXN2 (Clontech) (Gene 108, 193-199, 1991) (FIG. 2B) to prepare rat regucalcin expression vector RC/pCXN2. Said RC/pCXN2 was resected with SalI, SfiI and MluI to obtain a linealized 3.6 kbp fragment (FIG. 3).

(Preparation of Transgenic Rats)

The microinjection to rat prenuclear fertilized egg of 3.6 kbp DNA fragment solution linealized as described above was conducted as follows. A 4-weeks-old Sprague-Dawley (SD) female rat was raised in a light-dark cycle for 12 hours (light hours 4:00-16:00), at a temperature approximately of 23° C., a humidity approximately of 55%, and the female estrous cycle was observed by vaginal smear method, and the hormone treatment day was selected. 150 IU/kg of a pregnant horse serum gonadotrope (Nippon Zenyaku "PMS Zenyaku") was administered intraperitoneally to a female rat to perform superovulation. 48 hours later, 150 IU/kg of human placental gonadotrope (Sankyo Yell "PUBEROGEN") was administered intraperitoneally, and intercrossed with a male by cohabiting. 32 hours after the administration of human placental gonadotrope, prenuclear fertilized egg was collected by tubal superfusion.

The 3.6 kbp DNA fragment solution (concentration of 5 ng/μl) were microinjected to a male pronucleus of fertilized egg of Wistar rats thus generated. The egg to which DNA fragment is injected was cultured overnight by using m-KRB (m-Krebs Ringer buffer solution) medium in $CO_2$ incubator. The development get through 2-cell phase on the next day, 2-cell phase embryo with no abnormality were transplanted into uterine tubes of 9 foster parents (pseudopregnant female rat intercrossed with male wherein deferent canal is ligated) at a rate of 20-30 per rat, and 29 rats were generated. DNA was collected from tails of 27 rats that were generated and were alive until being 4-weeks old. The DNA collected were determined by PCR with the use of primer huRC-1; GGAGGCTATGTTGCCACCATTGGA (Seq. ID. No. 3); primer huRC-2; CCCTCCAAAGCAGCATGAAGTTG (Seq. ID. No. 4). As a result, the presence of the transgene was identified in a total of 5 rats (4 males and 1 female). Among these, 5 rats transmitted the transgene to the next generation.

Example 3

Ability to Suppress Weight Gain

Among strains of transgenic rats (heterozygote) obtained in Example 2, the strains which the amount of regucalcin expressed in tail tissue was largest were intercrossed to generate transgenic rat (homozygote). Furthermore, it was identified to be homozygote by determining the integration of transgene to genomic DNA extracted from rat tail tissue by PCR, and the integrated amount detected was more than 2 times of the cDNA amount of heterozygote. The ability of suppressing weight gain was examined by using said homozygote transgenic mouse. The average level of body weight of 3-4 weeks old wild-type SD rats and transgenic rats (homozygote) for 8 rats each are shown in Table 1. Student's t test, P<0.01, it is shown by mean value±S.E.M. so a significant difference is considered. It was verified that the weight gain is suppressed by the overexpression of regucalcin gene.

TABLE 1

| | body weight (g) |
|---|---|
| wild-type | 88.5 ± 3.8 |
| transgenic | 69.5 ± 2.4* |

Example 4

Animal Models Having Bone Pathology (SD Strain Homozygote Model Rats Having Bone Pathology)

Among strains of transgenic rats (heterozygote) obtained in Example 2, the strains which the amount of regucalcin expressed in tail tissue was largest were intercrossed to generate transgenic rat (homozygote). Furthermore, it was identified to be homozygote by determining the integration of transgene to genomic DNA extracted from rat tail tissue by PCR, and the integrated amount detected was more than 2 times of the cDNA amount of heterozygote. Among homozygote transgenic rat having apparently no bone pathology described above, male and female rats living stable through many generations were used as SD strain model rats having bone pathology of test group (homozygote), to perform morphological measurement estimation of bone (bone density, bone strength, bone thickness of diaphyseal cortex and length of surrounding of cortex) and biochemical measurement estimation of bone component (amount of calcium, alkaline phosphatase activity which is the marker enzyme of osteoblast and amount of DNA which is the index of the number of cells in bone tissues). Male and female SD strain wild-type normal rats were used as control. In the meantime, for each measurement estimation, 5 rats were used for each group in test group as well as in control, each measurement value was shown by mean value±S.M.E., statistic significant difference was detected by Student's t-test, and under P<0.01 (1%) was determined as with significant difference.

(Morphological Measurement Estimation of Bone)

5-6 weeks-old female and male SD strain model rats having bone pathology (test group) and SD strain wild-type normal rat (control) were dissected under etherization to isolate femur tissue, muscle tissue were removed, and submerged completely in 70% ethanol solution until providing for a prescribed measurement to obtain the sample. Said samples were scanned in 5 sites, at a slice width of 0.5 mm from 2.0 mm site from distal epiphysis in metaphysis (growth plate cartilage) by using pQTC bone density measurement apparatus for animal research (XCT Research SA+: Stratec Medizintecnik GmbH Pforzhein Germany). Approximately ½ site of bone length was made to be diaphysis site, and scanning was performed for 1 part. The results of scanning are shown in Table 5 (test group: the upper and medium column are for the metaphysis part; the left of the bottom column is the diaphysis part) and Table 6 (control group: the upper and medium column are for the metaphysis part; the left of the bottom column is the diaphysis part). After the scanning, the bone density, bone strength of diaphysis and metaphysis, bone thickness of diaphyseal cortex and length of surrounding outer membrane of cortex in diaphysis tissue for each group were automatically calculated and shown. The results are shown in Tables 2 to 5, respectively. In the meantime, in Table 6, the measurement parameters and analysis parameters for PQTC described above are shown.

As a result of pQTC measurement, the bone density decreased in model rats having bone pathology compared to normal rats, both for male and female, but significantly for females (Table 2). As for bone strength, comparing with male normal rats, the bone strength for model rats having bone pathology is lowered, but for female, it has been clear that the bone strength for model rats having bone pathology lowered down to 40 to 45% of normal rats in diaphysis as well in metaphysis part (Table 3). As for the cortex of diaphysis part (cortical bone) tissue, the bone thickness was lowered significantly in model rats having bone pathology, comparing with normal rats, for both male and female (Table 4). As for the length of surrounding outer membrane of cortex in diaphysis tissue (cortical bone), there were no significant differences for males between the 2 groups, but as for females, the length of surrounding outer membrane of cortex lowered significantly for model rats having bone pathology comparing with normal rats (Table 5).

TABLE 2

| bone density of bone tissue (mg/cm$^3$) | | | |
|---|---|---|---|
| | | diaphysis part (mg/cm$^3$) | metaphysis part (mg/cm$^3$) |
| male | wildtype | 494.3 ± 12.94 | 345.8 ± 12.25 |
| | transgenic | 425.0 ± 31.28* | 304.4 ± 19.69* |
| female | wildtype | 465.8 ± 15.05 | 388.0 ± 18.77 |
| | transgenic | 215.0 ± 5.38* | 274.6 ± 7.82* |

TABLE 3

| bone strength of bone tissue (mm$^3$) | | | |
|---|---|---|---|
| | | diaphysis part (mm$^3$) | metaphysis part (mm$^3$) |
| male | wild-type | 2.794 ± 0.127 | 3.426 ± 0.077 |
| | transgenic | 2.368 ± 0.308 | 3.012 ± 0.394 |
| female | wildtype | 2.446 ± 0.063 | 3.194 ± 0.102 |
| | transgenic | 1.163 ± 0.029* | 1.298 ± 0.108* |

TABLE 4

| thickness of cortial bone of diaphysis (cortical bone) tissue (mm) | | |
|---|---|---|
| | | diaphysis part (mm) |
| male | wild-type | 0.309 ± 0.012 |
| | transgenic | 0.112 ± 0.016* |
| female | wild-type | 0.337 ± 0.012 |
| | transgenic | 0.257 ± 0.040* |

TABLE 5 length of surrounding outer membrane of cortex in diaphysis tissue (mm)

|  |  | diaphysis part (mm) |
|---|---|---|
| male | wild-type | 9.365 ± 0.183 |
|  | transgenic | 9.540 ± 0.175 |
| female | wild-type | 9.004 ± 0.096 |
|  | transgenic | 8.761 ± 0.234* |

TABLE 6 measurement parameter and measurement site

| slice thickness | 500 μm | position of reference | the end part of femur is indicated by SV image |
| --- | --- | --- | --- |
| voxel size | 80 μm | measurement site: metaphysis part (cancellous bone) | total of 5 slices 5.0 mm thick, 2.0 mm site from distal end |
|  | 80 μm | measurement site: diaphysis part (cortical part) | approximately 1/2 of bone length |
| measurement time |  | 7 min. per sample | (including SV scan) |

| analysis parameter | | | |
| --- | --- | --- | --- |
| CALCBD | | CORTBD (SSI) | |
| counter mode: 2 | peel mode: 2 | cortical mode: 1 | |
| thershold | — Trabecular area thershold 395 mg/cm$^3$ | thershold inner thershold | 690/(&464) mg/cm$^3$ |

(Biochemical Measurement Estimation of Bone Component)

5-6 weeks-old female and male SD homogeneous strain model rats having bone pathology (test group) and SD strain wild-type normal rat (control) were dissected under etherization to isolate femur tissue, muscle tissue were removed, and submerged completely in 70% ethanol solution until providing for a prescribed measurement to obtain the sample. Said sample was divided into diaphysis part (cortical bone) and metaphysis part (cancellous bone), and amount of calcium, alkaline phosphatase activity which is the marker enzyme of osteoblast and amount of DNA which is the index of the number of cells in bone tissues were measured.

The measurement of the amount of calcium in bone tissues (mg/g bone dry weight) was performed by ashing the diaphysis part (cortical bone) and metaphysis part (cancellous bone) at 640° C. for 24 hours, by measuring the weight, then dissolved in 6N hydrochloric acid to measure the amount of bone calcium with an atomic absorption. The results of the amount of calcium in bone tissues represented by mg/g bone dry weight are shown in Table 7. As it is shown in Table 7, the amount of bone calcium in model rats having bone pathology were lowered significantly in both male and female, comparing to normal rats. Especially in female, the lowering of the amount of bone calcium was notable.

TABLE 7

Amount of calcium in bone tissue (mg/g bone dry weight)

|  |  | diaphysis part | metaphysis part |
| --- | --- | --- | --- |
| male | wildtype | 217.6 ± 4.47 | 169.1 ± 3.99 |
|  | transgenic | 192.0 ± 7.89* | 142.5 ± 2.46* |
| female | wildtype | 219.4 ± 3.51 | 185.4 ± 8.55 |
|  | transgenic | 174.4 ± 4.69* | 137.3 ± 8.54* |

For the measurement of alkaline phosphatase activity in bone tissues, the diaphysis part (cortical bone) and metaphysis part (cancellous bone) were submerged in ice-cooled 3 ml of 6.5 mM partial buffer solution (pH 7.4), cut into small pieces, homogenized in a Potter-Elvehjem homogenizer with a Teflon pestle, and destructed by using a supersonic apparatus for 60 seconds. The homogenate was centrifuged at 600 rpm for 5 minutes, and the resultant supernatant was used for the measurement of enzyme activity. The alkaline phosphatase activity was determined by the method of Walter and Schutt (Bergmeyer HU (ed) Methods of enzymatic analysis, Vol. 1-2, Academic Press, New York, PP 856-860, 1965). Protein concentration was determined by the method of Lowry et al. (J. Biol. Chem., 193, 265-273, 1951). The results showing the alkaline phosphatase activity in bone tissues represented in □mol/min/mg protein of released p-nitrophenol are shown in Table 8. From Table 8, as for model rats having bone pathology, comparing with normal rats, for the diaphysis part (cortical bone) the alkaline phosphatase activity was increasing significantly in male, and for metaphysis part (cancellous bone) the alkaline phosphatase activity was increasing significantly in female.

TABLE 8 alkaline phosphatase activity in bone tissues (μmol/min/mg protein)

|  |  | diaphysis part | metaphysis part |
| --- | --- | --- | --- |
| male | wildtype | 1.467 ± 0.072 | 1.246 ± 0.038 |
|  | transgenic | 1.104 ± 0.093* | 1.204 ± 0.038 |
| female | wildtype | 1.192 ± 0.076 | 1.355 ± 0.029 |
|  | transgenic | 1.067 ± 0.095 | 1.107 ± 0.011* |

For the measurement of the amount of DNA in bone tissues, the diaphysis part (cortical bone) and metaphysis part (cancellous bone) were submerged in ice-cooled 3 ml of 6.5 mM partial buffer solution (pH 7.4) respectively, cut into small pieces, and shakes in ice-cooled 4.0 ml of 0.1 N sodium hydroxide solution for 24 hours. After the alkaline extraction and centrifugation at 10,000 rpm for 5 minutes, the resultant supernatant was used for DNA amount determination. DNA amount was determined by the method of Ceriotti (J. Biol. Chem., 214, 39-77, 1955). The results showing the DNA amount in bone tissue represented in mg/g bone tissue wet weight are shown in Table 9. As it is shown in Table 9, comparing with normal rats, in model rats having bone pathology, in the diaphysis part (cortical bone) DNA amount was lowered significantly in female, and for metaphysis part (cancellous bone), DNA amount was lowered significantly both in male and female.

TABLE 9

| | | amount of DNA in bone tissues (mg/g bone tissue wet weight) | |
|---|---|---|---|
| | | diaphysis part | metaphysis part |
| male | wildtype | 2.55 ± 0.13 | 4.64 ± 0.29 |
| | transgenic | 2.99 ± 0.24 | 3.19 ± 0.22* |
| female | wild-type | 2.40 ± 0.31 | 4.39 ± 0.40 |
| | transgenic | 1.26 ± 20.18* | 2.37 ± 0.38* |

As it is described above, as for the animal model having bone pathology of the present invention, a clear bone change was found for femur tissue. Said bone change were observed in both diaphysis part (cortical bone) and metaphysic part (cancellous bone), morphologically and biochemically (bone component). It has been revealed that the bone change is based on the bone resorption (bone mineral dissolution) by bone tissue and impairment of bone formation. Especially, said bone change was more significant in male more than in female. Moreover, as for the animal model having bone pathology of the present invention, it is verified that the characteristic of bone pathology is stable through many generations.

FURTHER DESCRIPTION OF THE INVENTION

The invention will now be further described by the following numbered paragraphs:

1. A transgenic non-human animal to which a regucalcin gene is introduced and which overexpresses regucalcin.

2. The transgenic non-human animal according to paragraph 1, wherein straight chain DNA which is arranged in the order of cytomegalovirus-IE enhancer, chicken β-actin promoter, regucalcin gene, rabbit β-glovin poly A signal is introduced.

3. The transgenic non-human animal according to paragraph 1 or 2, wherein the regulcaltin gene is a gene that encodes protein consisting of amino acid sequence of Seq. ID No. 2 of the sequence listing.

4. The transgenic non-human animal according to paragraph 3, wherein the gene encoding protein consisting of amino acid sequence of Seq. ID No. 2 of the sequence listing is, a rat regucalcin gene consisting of DNA sequence of Seq. ID No. 1 of the sequence listing.

5. The transgenic non-human animal according to any of paragraphs 1 to 4, wherein the animal is homozygote.

6. The transgenic non-human animal according to any of paragraphs 1 to 5, wherein the animal has an ability to suppress the weight gain.

7. The transgenic non-human animal according to any of paragraphs 1 to 6, wherein the animal is susceptible to dysfunction of cerebrum.

8. The transgenic non-human animal according to any of paragraphs 1 to 7, wherein the animal is susceptible to insulin independent diabetes.

9. The transgenic non-human animal according to any of paragraphs 1 to 8, wherein the animal is susceptible to renal hypertension.

10. The transgenic non-human animal according to any of paragraphs 1 to 9, wherein the animal is susceptible to impairment of tubular reabsorption.

11. The transgenic non-human animal according to any of paragraphs 1 to 10, wherein the non-human animal is a rat.

12. A method for producing regucalcin, wherein the transgenic non-human animal according to any of paragraphs 1 to 11 is used.

13. A screening method of preventive and therapeutic agents for diseases caused by the overexpression of regucalcin, wherein the transgenic non-human animal according to any of paragraphs 1 to 11, or tissues, organs or cells derived from the transgenic non-human animal and a test substance are used.

14. The screening method of preventive and therapeutic agents for diseases caused by the overexpression of regucalcin according to paragraph 13, wherein the test substance is administered to the transgenic non-human animal, and the level of the weight gain of said transgenic non-human animal is measured and estimated.

15. The screening method of preventive and therapeutic agents for diseases caused by the overexpression of regucalcin according to paragraph 13 or 14, wherein the disease caused by the overexpression of regucalcin is dysfunction of cerebrum.

16. The screening method of preventive and therapeutic agents for diseases caused by the overexpression of regucalcin according to paragraph 13 or 14, wherein the disease caused by the overexpression of regucalcin is insulin independent diabetes.

17. The screening method of preventive and therapeutic agents for diseases caused by the overexpression of regucalcin according to paragraph 13 or 14, wherein the disease caused by the overexpression of regucalcin is renal hypertension.

18. The screening method of preventive and therapeutic agents for diseases caused by the overexpression of regucalcin according to paragraph 13 or 14, wherein the disease caused by the overexpression of regucalcin is impairment of tubular reabsorption.

19. A preventive or therapeutic agent for diseases caused by the overexpression of regucalcin obtained by the screening method according to any of paragraphs 13 to 18.

20. A screening method of causative agents of diseases caused by the lowering of regucalcin expression wherein the transgenic non-human animal according to any of paragraphs 1 to 11, or tissues, organs or cells derived from the transgenic non-human animal and a test substance are used.

21. The screening method of causative agents of diseases caused by the lowering of regucalcin expression according to paragraph 20, wherein the test substance is administered to the transgenic non-human animal, and the level of the weight loss of the transgenic non-human animal is measured and estimated.

22. The screening method of causative agents of diseases caused by the lowering of regucalcin expression according to paragraph 20 or 21, wherein the disease caused by the lowering of regucalcin expression is arteriosclerosis myocardial infarction.

23. The screening method of causative agents of diseases caused by the lowering of regucalcin expression according to paragraph 20 or 21, wherein the disease caused by the lowering of regucalcin expression is myocardial infarction.

24. A causing substrate of disease caused by the lowering of regucalcin expression obtained by the screening method according to any of paragraphs 20 to 23.

25. An animal model having bone pathology wherein the animal model is a non-human animal that overexpresses regucalcin and shows bone pathology.

26. The animal model having bone pathology according to paragraph 25, wherein the animal expresses one or more bone pathology of any of vulnerability of bone tissue, change of bone morphology or delay in bone growth.

27. The animal model having bone pathology according to paragraph 25 or 26, wherein the animal is selected and determined among non-human animal that overexpresses regucalcin by a morphological measurement estimation of bone and/or a biochemical measurement estimation of bone component.

28. The animal model having bone pathology according to paragraph 27, wherein the morphological measurement estimation of bone is one or more measurement estimations of any of bone density, bone strength, bone thickness of diaphyseal cortex or length of surrounding of cortex.

29. The animal model having bone pathology according to paragraph 27, wherein the biochemical measurement estimation of bone component is one or more measurement estimations of any of amount of calcium, alkaline phosphatase activity or amount of DNA in bone tissues.

30. The animal model having bone pathology according to any of paragraphs 25 to 29, wherein the characteristic of bone pathology is stable through many generations.

31. The animal model having bone pathology according to any of paragraphs 25 to 30, wherein the non-human animal that overexpresses regucalcin is a transgenic non-human animal to which regucalcin gene is introduced.

32. The animal model having bone pathology according to any of paragraphs 26 to 32, wherein the non-human animal that overexpresses regucalcin is homozygote.

33. The animal model having bone pathology according to any of paragraphs 25 to 32, wherein the non-human animal that overexpresses regucalcin is a female non-animal.

34. The animal model having bone pathology according to any of paragraphs 25 to 33, wherein the non-human animal that overexpresses regucalcin is a rat.

35. A screening method of preventive and therapeutic agents for bone diseases wherein a test substance is administered to a animal model having bone pathology according to any of paragraphs 25 to 34, and a morphological measurement estimation of bone and/or a biochemical measurement estimation of bone component of said animal model having bone pathology are performed.

36. The screening method of preventive and therapeutic agents for bone disease according to paragraph 35, wherein the morphological measurement estimation of bone is one or more measurement estimations of any of bone density, bone strength, bone thickness of diaphyseal cortex or length of surrounding of cortex.

37. The screening method of preventive and therapeutic agents for bone disease according to paragraph 35, wherein the biochemical measurement estimation of bone component is one or more measurement estimations of any of amount of calcium, alkaline phosphatase activity or amount of DNA in bone tissues.

38. The screening method of preventive and therapeutic agents for bone disease according to any of paragraphs 35 to 37, wherein the bone disease is aosteoporosis.

39. A preventive or therapeutic agent for bone disease obtained by the screening method according to any of paragraphs 35 to 38.

INDUSTRIAL APPLICABILITY

The regucalcin transgenic non-human animal of the present invention, especially the regucalcin transgenic rat, is useful for animal model for evaluating pathology such as adult diseases, lifestyle-related disease, geriatric disease and the like related to $Ca^{2+}$ signaling, such as impairment of liver, renal disorder, diabetes, myocardial infarction, hypertension, Alzheimer's disease and the like. Moreover, the regucalcin is regulating cell function related to intracellular $Ca^{2+}$ signaling, and as the regucalcin transgenic non-human animal of the present invention overexpresses said regucalcin, the animal can be a useful means as animal model for developing therapeutic drugs for gene therapy for repair/improvement of diseases specific to organs (cancer of liver, myocardial infarction, cerebrum dementia). Furthermore, the animal model having bone disease of the present invention can be used advantageously as a animal model having disease for treatment of bone disease such as osteoporosis and the like for preclinical study and the like for the purpose of the clarification of the bone pathology mechanism or the development of a new drug.

The invention claimed is:

1. A transgenic rat whose genome comprises a homozygous insertion of a cDNA sequence encoding a rat regucalcin operably linked to a promoter, wherein said transgenic rat over expresses regucalcin and said rat exhibits a decrease in any one or more of bone density, bone strength, and bone thickness of diaphyseal cortex or length of surrounding of cortex.

2. The transgenic rat of claim 1, wherein the rat that overexpresses regucalcin is a female rat.

* * * * *

SEQUENCE LISTING

<160> NUMBER OF SEQ ID NOS: 4

<210> SEQ ID NO 1
<211> LENGTH: 900
<212> TYPE: DNA
<213> ORGANISM: Rattus norvegicus
<220> FEATURE:
<221> NAME/KEY: CDS
<222> LOCATION: (1)..(897)

<400> SEQUENCE: 1 atg tct tcc atc aag att gaa tgt gtt tta agg gag aac tac agg tgt         48

```
                Met Ser Ser Ile Lys Ile Glu Cys Val Leu Arg Glu Asn Tyr Arg Cys
                  1               5                  10                  15 ggg gag tcc cct gtg tgg gag gag gca tca aag tgt ctg ctg ttt gta                 96
Gly Glu Ser Pro Val Trp Glu Glu Ala Ser Lys Cys Leu Leu Phe Val
                 20                  25                  30 gac atc cct tca aag act gtc tgc cga tgg gat tcg atc agc aat cga                144
Asp Ile Pro Ser Lys Thr Val Cys Arg Trp Asp Ser Ile Ser Asn Arg
             35                  40                  45 gtg cag cga gtt ggt gta gat gcc cca gtc agt tca gtg gca ctt cga                192
Val Gln Arg Val Gly Val Asp Ala Pro Val Ser Ser Val Ala Leu Arg
         50                  55                  60 cag tca gga ggc tat gtt gcc acc att gga acc aag ttc tgt gct ttg                240
Gln Ser Gly Gly Tyr Val Ala Thr Ile Gly Thr Lys Phe Cys Ala Leu
 65                  70                  75                  80 aac tgg gaa gat caa tca gta ttt atc cta gcc atg gtg gat gaa gat                288
Asn Trp Glu Asp Gln Ser Val Phe Ile Leu Ala Met Val Asp Glu Asp
                 85                  90                  95 aag aaa aac aat cga ttc aat gat ggg aag gtg gat cct gct ggg aga                336
Lys Lys Asn Asn Arg Phe Asn Asp Gly Lys Val Asp Pro Ala Gly Arg
            100                 105                 110 tac ttt gct ggt acc atg gct gag gaa acc gcc cca gct gtt ctg gag                384
Tyr Phe Ala Gly Thr Met Ala Glu Glu Thr Ala Pro Ala Val Leu Glu
        115                 120                 125 cgg cac caa ggg tcc ttg tac tcc ctt ttt cct gat cac agt gtg aag                432
Arg His Gln Gly Ser Leu Tyr Ser Leu Phe Pro Asp His Ser Val Lys
    130                 135                 140 aaa tac ttt aac caa gtg gat atc tcc aat ggt ttg gat tgg tcc ctg                480
Lys Tyr Phe Asn Gln Val Asp Ile Ser Asn Gly Leu Asp Trp Ser Leu
145                 150                 155                 160 gac cat aaa atc ttc tac tac att gac agc ctg tcc tac act gtg gat                528
Asp His Lys Ile Phe Tyr Tyr Ile Asp Ser Leu Ser Tyr Thr Val Asp
                165                 170                 175 gcc ttt gac tat gac ctg cca aca gga cag att tcc aac cgc agg act                576
Ala Phe Asp Tyr Asp Leu Pro Thr Gly Gln Ile Ser Asn Arg Arg Thr
            180                 185                 190 gtt tac aag atg gaa aaa gat gaa caa atc cca gat gga atg tgc att                624
Val Tyr Lys Met Glu Lys Asp Glu Gln Ile Pro Asp Gly Met Cys Ile
        195                 200                 205 gat gtt gag ggg aag ctt tgg gtg gcc tgt tac aat gga gga aga gta                672
Asp Val Glu Gly Lys Leu Trp Val Ala Cys Tyr Asn Gly Gly Arg Val
    210                 215                 220 att cgc cta gat cct gag aca ggg aaa aga ctg caa act gtg aag ttg                720
Ile Arg Leu Asp Pro Glu Thr Gly Lys Arg Leu Gln Thr Val Lys Leu
225                 230                 235                 240 cct gtt gat aaa aca act tca tgc tgc ttt gga ggg aag gat tac tct                768
Pro Val Asp Lys Thr Thr Ser Cys Cys Phe Gly Gly Lys Asp Tyr Ser
                245                 250                 255 gaa atg tac gtg aca tgt gcc agg gat ggg atg agc gcc gaa ggt ctt                816
Glu Met Tyr Val Thr Cys Ala Arg Asp Gly Met Ser Ala Glu Gly Leu
            260                 265                 270 ttg agg cag cct gat gct ggt aac att ttc aag ata aca ggt ctt ggg                864
Leu Arg Gln Pro Asp Ala Gly Asn Ile Phe Lys Ile Thr Gly Leu Gly
        275                 280                 285 gtc aaa gga att gct cca tat tcc tat gca ggg taa                                900
Val Lys Gly Ile Ala Pro Tyr Ser Tyr Ala Gly
    290                 295

<210> SEQ ID NO 2
<211> LENGTH: 299
<212> TYPE: PRT
```

<213> ORGANISM: Rattus norvegicus

<400> SEQUENCE: 2

```
Met Ser Ser Ile Lys Ile Glu Cys Val Leu Arg Glu Asn Tyr Arg Cys
  1               5                  10                  15
Gly Glu Ser Pro Val Trp Glu Ala Ser Lys Cys Leu Leu Phe Val
                 20                  25                  30
Asp Ile Pro Ser Lys Thr Val Cys Arg Trp Asp Ser Ile Ser Asn Arg
             35                  40                  45
Val Gln Arg Val Gly Val Asp Ala Pro Val Ser Ser Val Ala Leu Arg
     50                  55                  60
Gln Ser Gly Gly Tyr Val Ala Thr Ile Gly Thr Lys Phe Cys Ala Leu
 65                  70                  75                  80
Asn Trp Glu Asp Gln Ser Val Phe Ile Leu Ala Met Val Asp Glu Asp
                 85                  90                  95
Lys Lys Asn Asn Arg Phe Asn Asp Gly Lys Val Asp Pro Ala Gly Arg
            100                 105                 110
Tyr Phe Ala Gly Thr Met Ala Glu Glu Thr Ala Pro Ala Val Leu Glu
            115                 120                 125
Arg His Gln Gly Ser Leu Tyr Ser Leu Phe Pro Asp His Ser Val Lys
    130                 135                 140
Lys Tyr Phe Asn Gln Val Asp Ile Ser Asn Gly Leu Asp Trp Ser Leu
145                 150                 155                 160
Asp His Lys Ile Phe Tyr Tyr Ile Asp Ser Leu Ser Tyr Thr Val Asp
                165                 170                 175
Ala Phe Asp Tyr Asp Leu Pro Thr Gly Gln Ile Ser Asn Arg Arg Thr
            180                 185                 190
Val Tyr Lys Met Glu Lys Asp Glu Gln Ile Pro Asp Gly Met Cys Ile
            195                 200                 205
Asp Val Glu Gly Lys Leu Trp Val Ala Cys Tyr Asn Gly Gly Arg Val
    210                 215                 220
Ile Arg Leu Asp Pro Glu Thr Gly Lys Arg Leu Gln Thr Val Lys Leu
225                 230                 235                 240
Pro Val Asp Lys Thr Thr Ser Cys Cys Phe Gly Gly Lys Asp Tyr Ser
                245                 250                 255
Glu Met Tyr Val Thr Cys Ala Arg Asp Gly Met Ser Ala Glu Gly Leu
            260                 265                 270
Leu Arg Gln Pro Asp Ala Gly Asn Ile Phe Lys Ile Thr Gly Leu Gly
            275                 280                 285
Val Lys Gly Ile Ala Pro Tyr Ser Tyr Ala Gly
    290                 295
```

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer huRC-1

<400> SEQUENCE: 3
ggaggctatg ttgccaccat tgga                                       24

<210> SEQ ID NO 4
<211> LENGTH: 23
<212> TYPE: DNA
<213> ORGANISM: Artificial Sequence

```
<220> FEATURE:
<223> OTHER INFORMATION: Description of Artificial Sequence: Synthetic
      primer huRC-2

<400> SEQUENCE: 4
ccctccaaag cagcatgaag ttg                                              23
```